United States Patent [19]

Akimoto et al.

[11] Patent Number: 5,320,837
[45] Date of Patent: Jun. 14, 1994

[54] CONTROLLED RELEASE PREPARATIONS OF ACTIVE MATERIALS

[75] Inventors: Shin-ichi Akimoto; Susumu Honda, both of Tokyo; Tohru Yasukohchi, Kanagawa, all of Japan

[73] Assignee: Nippon Oil and Fats Co., Ltd., Tokyo, Japan

[21] Appl. No.: 763,831

[22] Filed: Sep. 23, 1991

Related U.S. Application Data

[62] Division of Ser. No. 168,040, Mar. 14, 1988, Pat. No. 5,081,111.

[30] Foreign Application Priority Data

Mar. 14, 1987 [JP] Japan .................................. 62-57926

[51] Int. Cl.$^5$ ........................ A61K 31/74; C08F 34/02
[52] U.S. Cl. ................... 424/78.19; 424/78.21; 424/484; 424/485
[58] Field of Search .................. 424/78, 78.21, 78.19, 424/484, 485, 94.1; 525/285; 526/271, 272, 1, 327.7

[56] References Cited

FOREIGN PATENT DOCUMENTS 56-133334 10/1981 Japan .
59-104323 6/1984 Japan .

OTHER PUBLICATIONS

Takaheshi et al. (1984), Biochemical and Biophysical Res. Comm., vol. 121, 261-265.

N.Y. Acad. Sciences (1985), pp. 160-181.

Primary Examiner—Thurman K. Page
Assistant Examiner—Raj Bawa
Attorney, Agent, or Firm—Sughrue, Mion, Zinn, Macpeak & Seas

[57] ABSTRACT

A controlled release preparation of an active material comprising a reaction product obtained by reacting (a) a copolymer consisting essentially of maleic anhydride and at least one polyalkylene glycol ether represented by formula (I):

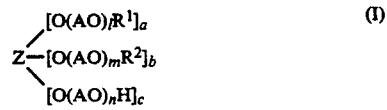

wherein B represents a residue of a compound having from 2 to 8 hydroxyl groups; $R^1$ represents an alkenyl group having from 2 to 5 carbon atoms; AO represents an oxyalkylene group having from 2 to 18 carbon atoms or a combination thereof which may be linked together in blocks or at random; $R^2$ represents a hydrocarbon group having from 1 to 24 carbon atoms; a represents a positive integer, b and c each represents 0 or a positive integer, and $a+b+c=2$ to 8; $l \geq 0$, $m \geq 0$, $n \geq 0$, and $l+m+n = 1$ to 1000; and (b) an active material. The preparation is soluble both in water and in an organic solvent and exhibits activity for a prolonged period of time.

5 Claims, No Drawings

CONTROLLED RELEASE PREPARATIONS OF ACTIVE MATERIALS

This is a divisional of application Ser. No. 07/168,040 filed Mar. 14, 1988, now U.S. Pat. No. 5,081,111, issued Jan. 14, 1992.

FIELD OF THE INVENTION

This invention relates to an active material releasing preparation which gradually releases an active material, such as perfumes, growth regulating substances, pheromones, hormones, vitamines, glycosides, enzymes, aminoglucosides, pesticides, etc. More particularly, it relates to an active material releasing preparation for sustained release of an active material while controlling rapid deactivation of the active material or to an active material releasing preparation in which solubility of the active material is changed so as to permit its use in a solvent that has never been applied.

BACKGROUND OF THE INVENTION

Various attempts have been made to control deactivation of an active material to make the release slow or to change solubility of an active ingredient. For instance, it has been proposed that volatile active materials, such as perfumes, can be modified by adsorption onto a porous substance, conversion to a clathrate compound thereof, entrapping in gel, or the like technique. These techniques do not involve chemical reaction of the active material.

On the other hand, it is known to obtain controlled release of an active material or to change solubility of an active material through chemical modification. For example, there have been proposed a process in which amino groups or carboxyl groups of proteins, such as enzymes, are reacted with a modified polyethylene glycol having a specific structure as disclosed in Japanese Patent Application (OPI) No. 104323/84 (the term "OPI" as used herein means "unexamined published Japanese patent application") and *Biochemical and Biophysical Research Communications*, Vol. 121, 261–265 (1984) as to reaction of amino groups, and in Japanese Patent Publication No. 7649/83 as to reaction of carboxyl groups; and a process in which amino groups of proteins are reacted with a copolymer having an acid anhydride group, e.g., an olefin-maleic anhydride copolymer, as reported in *Macromolecules as Drugs and as Carriers for Biologically Active Materials*, 160–181, The New York Academy of Sciences (1985).

SUMMARY OF THE INVENTION

The inventors have conducted studies on controlled release of an active material from a system obtained by chemical reaction of an active material. As a result, it has now been found that a reaction product obtained by reacting an active material with a copolymer of maleic anhydride and a copolymerizable polyalkylene glycol ether is soluble in water and/or an organic solvent and capable of slowly releasing the active material upon hydrolysis.

The present invention relates to a controlled release preparation of an active material comprising a reaction product obtained by reacting (a) a copolymer consisting essentially of maleic anhydride and at least one polyalkylene glycol ether represented by formula (I):

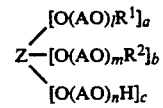

wherein B represents a residue of a compound having from 2 to 8 hydroxyl groups; $R^1$ represents an alkenyl group having from 2 to 5 carbon atoms; AO represents an oxyalkylene group having from 2 to 18 carbon atoms or a combination thereof which may be linked together in blocks or at random; $R^2$ represents a hydrocarbon group having from 1 to 24 carbon atoms; a represents a positive integer, b and c each represents 0 or a positive integer, and $a+b+c=2$ to 8; $l \geq 0$, $m \geq 0$, $n \geq 0$, and $l+m+n=1$ to 1000, and (b) an active material.

DETAILED DESCRIPTION OF THE INVENTION

In formula (I), alkenyl groups represented by $R^1$ include a vinyl group, an allyl group, a methallyl group, a 1,1-dimethyl-2-propenyl group, a 3-methyl-3-butenyl group, etc.

Compounds having 2 to 8 hydroxyl groups per molecule which provide the residue Z in formula (I) include polyhydric phenols such as catechol, resorcine, hydroquinone, and phloroglucine; polyhydric alcohols, such as ethylene glycol, propylene glycol, butylene glycol, dodecylene glycol, octadecylene glycol, neopentyl glycol, styrene glycol, glycerine, diglycerine, polyglycerine, trimethylolethane, trimethylolpropane, 1,3,5-pentanetriol, erythritol, pentaerythritol, dipentaerythritol, sorbitol, sorbitan, sorbide, a sorbitol-glycerine condensate, adonitol, arabitol, xylitol and mannitol; saccharides, such as xylose, arabinose, ribose, rhamnose, glucose, fructose, galactose, mannose, sorbose, cellobiose, maltose, isomaltose, trehalose, sucrose, raffinose, gentianose, and melezitose; and partial ethers or partial esters thereof.

Oxyalkylene groups represented by AO include an oxyethylene group, an oxypropylene group, an oxybutylene group, an oxytetramethylene group, an oxystyrene group, an oxydodecylene group, an oxytetradecylene group, an oxyhexadecylene group, an oxyoctadecylene group, etc.

Hydrocarbon groups represented by $R^2$ include a methyl group, an ethyl group, a propyl group, an isopropyl group, a butyl group, an isobutyl group, a tert-butyl group, an amyl group, an isoamyl group, a hexyl group, a heptyl group, a 2-ethylhexyl group, an octyl group, a nonyl group, a decyl group, an undecyl group, a dodecyl group, an isotridecyl group, a tetradecyl group, a hexadecyl group, an isohexadecyl group, an octadecyl group, an isooctadecyl group, an oleyl group, an octyldodecyl group, a dococyl group, a decyltetradecyl group, a benzyl group, a cresyl group, a butylphenyl group, a dibutylphenyl group, an octylphenyl group, a nonylphenyl group, a dodecylphenyl group, a dioctylphenyl group, a dinonylphenyl group, a styrenated phenyl group, etc. In formula (I) AOs in ( )l, ( )m, and ( )n, respectively, may be the same or different.

The copolymer which can be used in the present invention can be prepared by copolymerizing maleic anhydride and the polyalkylene glycol ether represented by formula (I) and, if desired, other copolymerizable monomers in the presence of a radical polymerization catalyst, e.g., benzoyl peroxide, azobisisobutyronitrile, etc. The copolymerization may be carried out in a solvent such as toluene. In case of using a liquid polyalkylene glycol ether, the use of solvent may be eliminated.

Other monomers which may be used include vinyl monomers which are copolymerizable with maleic anhydride and the polyalkylene glycol ether of formula (I). Specific examples of the vinyl monomers are acrylic acid, methacrylic acid, itaconic acid, crotonic acid, maleic acid; salts of these acids with a monovalent or divalent metal, ammonium or an organic amine, esters of these acids with an alcohol having from 1 to 24 carbon atoms, or esters of these acids with a polyoxyalkylene glycol; aromatic vinyl compounds such as styrene and methylstyrene; vinyl halides such as vinyl chloride and vinylidene chloride; olefins such as isobutylene and diisobutylene; vinyl acetate, acrylonitrile, acrylamide, and the like.

Active materials which are reacted with the above-described copolymers include compounds having a hydroxyl group and compounds having an amino group.

Examples of the compounds having a hydroxyl group include perfumes such as linalool, geraniol, citronellol, eugenol, benzyl alcohol, phenethyl alcohol, and cinnamic alcohol; growth regulating substances such as n-decanol, p-menthane-3,8-diol, gibberellin, cytokinin, indol-3-ethanol, etc.; pheromones such as 9-tetradecene-1-ol, 6-nonene-1-ol, and 6-methyl-5-heptene-1-ol, etc.; hormones such as oestradiol, testosterone, hydroxytestosterone, and cortisone; vitamines such as vitamines A, $B_6$ and C; glycosides such as saponine, anthocyan; and the like.

Examples of the compounds having an amino group include various enzymes, such as hydrolases (e.g., amylase, protease, cellulase, hemicellulase, lipase, pectinase, lysozyme, hesperidinase, anthocyanase, aminoacylase, urease, invertase, melibiase, dextranase, peptidase, ribonuclease, lactase, etc.), oxidoreductases (e.g., glucose oxidase, uricase, catalase, lipoxygenase, cytochrome C, peroxidase, etc.), isomerases (e.g., glucose isomerase, etc.), transferases (e.g., cyclodextrin glucosyltransferase, transaminase, etc.), and eliminases (e.g., aspartase, hyaluronidase, chondroitinase, etc.); other peptides; aminoglucosides; and pesticides, such as 3,5-dichloroaniline, and 2,6-dichloro-4-nitroaniline.

The reaction product of the copolymer and the active material can easily be obtained by mixing them in the presence or absence of a solvent under heating.

In the maleic anhydride-polyalkylene glycol ether copolymer according to the present invention, the maleic acid unit exists in the form of an acid anhydride. This acid anhydride unit functions to chemically react with a hydroxyl group, an amino group, etc. of the active material to form an ester linkage, an amide linkage, etc., while the polyalkylene glycol ether unit determines the form of the controlled active material release preparation, i.e., whether it is solid or liquid, and also determines solubility of the preparation in water or organic solvents. In more detail, when a polyalkylene glycol ether having an oxyethylene group is used in a high proportion, the resulting preparation is water soluble. When a polyalkylene glycol ether containing no or a slight amount of an oxyethylene group is used, the resulting preparation is water insoluble. In particular, the polyalkylene glycol ether of formula (I) having two or more alkenyl groups represented by $R^1$, which may be the same or different, provides a solid reaction product.

The controlled release preparation of the active material of this invention comprises a reaction product obtained by the chemical reaction between the maleic anhydride-polyalkylene glycol ether copolymer and the active material and releases the active material, slowly and continuously, upon being hydrolyzed. Further, solubility of the preparation in water or organic solvents can be determined by appropriately selecting solubility of the copolymer. Accordingly, the controlled release preparation of the active material of the invention makes it possible to markedly broaden the range of application of the active material.

The present invention is now explained in greater detail with reference to the preparation examples and the working examples, but it should be understood that the present invention is not deemed to be limited thereto.

PREPARATION EXAMPLE 1

| | |
|---|---|
| $CH_2=CHCH_2O(C_3H_6O)_5(C_2H_4O)_{15}CH_3$ | 1022 g (1 mol) |
| Maleic anhydride | 103 g (1.05 mol) |
| Benzoyl peroxide | 12 g (0.05 mol) |

The above components were dissolved in 1 l of toluene. The solution was transferred to a fournecked flask equipped with a condenser, an inlet for nitrogen, a thermometer, and a stirrer. The solution was stirred at 80°±2° C. for 7 hours in a nitrogen atmosphere to effect polymerization. The toluene and the unreacted maleic anhydride were removed from the reaction mixture by distillation under reduced pressure to obtain 980 g of a copolymer. The resulting copolymer was designated as Copolymer 1. Copolymer 1 was a viscous liquid and had a saponification value of 99.9.

PREPARATION EXAMPLE 2

| | |
|---|---|
| $CH_2=CHCH_2O(C_2H_4O)_{20}CH_2CH=CH_2$ | 96 g (0.1 mol) |
| $CH_2=\underset{\underset{CH_3}{\vert}}{C}CH_2O(C_2H_4O)_{20}C_{12}H_{25}$ | 1008 g (0.9 mol) |
| Maleic anhydride | 108 g (1.1 mol) |
| Benzoyl peroxide | 12 g (0.05 mol) |

The above components were subjected to polymerization reaction in the same manner as in Preparation Example 1. As the reaction proceeded, a polymer began to precipitate. After completion of the reaction, the reaction mixture was centrifuged to remove the toluene. The residual precipitate was washed successively with 300 ml of toluene and 500 ml of hexane and then vacuum dried at 60° C. for 10 hours to obtain 1010 g of a copolymer. The resulting copolymer, designated as Copolymer 2, had a saponification value of 103.

In the same way as for Copolymer 2, Copolymers 3 to 9 were prepared as shown in Table 1 below.

TABLE 1

| Copolymer No. | Polyalkylene Glycol Ether (mol) | | Maleic Anhydride (mol) | Other Comonomer (mol) | | Saponification Value |
|---|---|---|---|---|---|---|
| 1 | $CH_2=CHCH_2O(C_3H_6O)_5(C_2H_4O)_{15}CH_3$ | 1.0 | 1.0 | — | | 99.9 |
| 2 | $CH_2=CHCH_2O(C_2H_4O)_{20}CH_2CH=CH_2$ | 0.1 | 1.0 | — | | 103 |
|   | $CH_2=C(CH_3)CH_2O(C_2H_4O)_{20}C_{12}H_{25}$ | 0.9 | | | | |
| 3 | $CH_2=CHO\{(C_4H_8O)_2(C_2H_4O)_{10}\}C_4H_9$ | 0.2 | 1.0 | — | | 118 |
|   | $CH_2=CHCH_2O(C_2H_4O)_{20}CH_3$ | 0.8 | | | | |
| 4 | $CH_2=CHCH_2O(C_2H_4O)_{200}CH_2CH=CH_2$ | 0.1 | 1.0 | styrene | 1.0 | 197 |
|   | $CH_2=CHCH_2O(C_2H_4O)_{20}CH_3$ | 0.8 | | | | |
| 5 | $CH_2=CHCH_2O(C_2H_4O)_{15}$–C₆H₄–$C_9H_{19}$ | 0.2 | 1.0 | glycerin diallyl ether | 0.05 | 212 |
|   | $CH_2=C(CH_3)CH_2O(C_2H_4O)_{10}(C_3H_6O)_3CH_3$ | 0.75 | | | | |
| 6 | $CH_2=C(CH_3)CH_2O(C_2H_4O)_{15}CH_3$ | 0.97 | 1.0 | — | | 260 |
|   | $CH_2O(C_2H_4O)_5CH_2CH=CH_2$ / $CHO(C_2H_4O)_5CH_2CH=CH_2$ / $CH_2O(C_2H_4O)_5CH_2CH=CH_2$ | 0.03 | | | | |
| 7 | $CH_2=CHCH_2O(C_2H_4O)_{10}CH_3$ | 0.98 | 1.0 | pentaerythritol diallyl ether | 0.02 | 236 |
| 8 | $CH_2=CHCH_2O(C_3H_6O)_5(C_2H_4O)_5CH_3$ | 0.98 | 1.0 | — | | 202 |
|   | $C[CH_2O(C_2H_4O)_3CH_2CH=CH_2]_4$ | 0.02 | | | | |
| 9 | $CH_2=CHCH_2O(C_2H_4O)_{10}CH_3$ | 0.95 | 1.0 | hyxaglycerine diallyl ether | 0.05 | 230 |

Note: The oxyalkylene groups in the braces { } are linked at random.

EXAMPLE 1

In 300 ml of pyridine was dissolved 110 g of Copolymer 1, and 10 g of β-phenethyl alcohol (0.,41 equivalent to the saponification value of Copolymer 1) was added thereto, then refluxed for 4 hours to obtain 110 g of an ester of Copolymer 1 and β-phenethyl alcohol.

Similarly, each of Copolymers 2 to 9 was esterified using β-phenethyl alcohol in an amount of 0.41 equivalent to the saponification value of the corresponding copolymer.

In 20 g of a 50 wt % methanolic aqueous solution was dissolved 0.2 g of each of the resulting copolymer esters, and the solution was put in a petri dish of 10 cm diameter and allowed to stand in a thermostat at 50° C. for 24 hours. Then, the solution remaining in the petri dish was dissolved in 20 g of a 50 wt % methanol aqueous solution having dissolved therein 0.2 g of sodium hydroxide, then refluxed for 1 hour. The β-phenethyl alcohol (a) in the resulting solution was quantitatively determined by gas chromatography. Separately, 0.2 g of the copolymer ester was dissolved in 20 g of a 50 wt % methanol aqueous solution having 0.2 g of sodium hydroxide dissolved therein, followed by refluxed for 1 hour, and then the β-phenethyl alcohol (b) in the solution was quantitatively determined. The percentage of the residual active material, β-phenethyl alcohol, was calculated by dividing (a) by (b).

For comparison, the same procedure as the above was repeated by using 0.02 g of β-phenethyl alcohol to which 0.18 g of polyoxyethylene (10 mols) nonylphenyl ether or 0.18 g of polyacrylamide is added.

The results obtained as shown in Table 2 below. It can be seen from the Table that the active material-copolymer preparation according to the present invention exhibits excellent persistency of activity.

TABLE 2

| Copolymer | Retention (%) | Remark |
|---|---|---|
| 1 | 48.5 | Invention |
| 2 | 51.3 | " |
| 3 | 49.5 | " |
| 4 | 50.0 | " |
| 5 | 48.7 | " |
| 6 | 51.5 | " |
| 7 | 52.3 | " |
| 8 | 51.6 | " |
| 9 | 51.4 | " |
| Polyoxyethylene (10 mols) nonylphenyl ether | 3.5 | Comparison |
| Polyacrylamide | 7.5 | " |

EXAMPLE 2

In the same manner as in Example 1, an ester formed between each of Copolymers 1 to 9 and geraniol was prepared, and the percentage of the residual active material was determined. For comparison, a composition of geraniol and polyoxyethylene (20 mols) sorbitan monooleate or polyacrylamide was evaluated in the same manner. The results obtained are shown in Table 3 below. As is apparent from Table 3, the active material-copolymer preparation according to the present invention exhibits excellent persistency of activity.

TABLE 3

| Copolymer | Retention (%) | Remark |
|---|---|---|
| 1 | 39.7 | Invention |
| 2 | 42.4 | " |
| 3 | 40.6 | " |
| 4 | 41.8 | " |
| 5 | 39.6 | " |
| 6 | 40.9 | " |
| 7 | 41.4 | " |
| 8 | 42.3 | " |
| 9 | 41.7 | " |
| Polyoxyethylene (20 mols) nonylphenyl ether | 2.4 | Comparison |
| Polyacrylamide | 5.8 | " |

EXAMPLE 3

In 300 ml of pyridine was dissolved 50 g of Copolymer 8, and 18 g of 2,6-dichloro-4-nitroaniline was added to the solution. The solution was heated under reflux for 4 hours, followed by concentration to a half volume. To the concentrate was added 300 ml of n-hexane while cooling in order to form a precipitate. The precipitate was collected by filtration and dried to recover an amide of Copolymer 8 and 2,6-dichloro-4-nitroaniline.

Ten grams of the resulting amide was charged in a 500-ml flask, and 100 ml of a 20% ethanolic aqueous solution having 0.1 g of sodium hydroxide dissolved therein was added thereto. After the mixture was boiled for 30 minutes, the liquid portion was removed. Then, 100 ml of a fresh ethanolic aqueous solution having the same composition as the above was added thereto, the mixture boiled for 30 minutes, and the liquid removed. This operation was repeated additional four times to obtain five liquid fractions 1 to 5.

For comparison, the same procedure was repeated, except for replacing the amide of Copolymer 8 with 3 g of 2,6-dichloro-4-nitroaniline adsorbed onto 50 g of polystyrene for chromatography.

The residual 2,6-dichloro-4-nitroaniline in each liquid fraction was determined by ultraviolet spectroscopy, and its ratio (%) to the initial amount of 2.7-dichloro-4-nitroaniline was calculated. The results obtained are shown in Table 4. As can be seen from the results in Table 4, the controlled release preparation of active material according to the present invention exhibits excellent persistency of activity.

TABLE 4

| Liquid Fraction No. | Residual Active Material | |
|---|---|---|
| | Invention | Comparison |
| 1 | 25.0 | 91.0 |
| 2 | 17.5 | 8.8 |
| 3 | 13.4 | 0.2 |
| 4 | 11.6 | 0 |
| 5 | 9.5 | 0 |

EXAMPLE 4

To 4 ml of a 0.2M borate buffer (pH 8.5) containing 20 mg of horseradish peroxidase was added 200 mg of Copolymer 3 and stired at 25° C. for 30 minutes. To the reaction mixture was added 100 ml of phosphate buffered saline (pH 7.0) cooled to 0° C., in order to stop the reaction. Any unreacted copolymer was removed from the reaction mixture by filtration through Diaflo Membrane A-50T (produced by Ulvac Service Co., Ltd.), and the residue was dried to obtain 170 mg of a modified peroxidase.

The degree of modification of the resulting peroxidase was determined in accordance with the method described in *Analytical Biochemicstry*, Vol. 14, 328–336 (1966). As a result, it was found that 60% of the total amino groups in the peroxidase had been modified with Copolymer 3.

Further, the resulting modified peroxidase was quite soluble not only in water but even in benzene, toluene, chloroform, and trichloroethane in each of which unmodified peroxidase is insoluble.

Activity of the modified peroxidase in water and benzene was determined by using hydrogen peroxide and o-phenylenediamine as substrates, and the results being shown in Table 5, in which the activity of unmodified peroxidase in water was taken as a standard (100).

TABLE 5

| Active Material | Relative Activity of Peroxidase | |
|---|---|---|
| | in Water | in Benzene |
| Unmodified peroxidase | 100 | 0 |
| Modified peroxidase | 70 | 45 |

It can be seen that the peroxidase preparation modified with the copolymer according to the present invention has solubility in each water and benzene and exhibits activity therein, indicating that the modification with the copolymer greatly improves properties of the unmodified enzyme.

While the invention has been described with reference to the specific embodiments thereof, it will be apparent to one skilled in the art that various changes and modifications can be made therein without departing from the spirit and scope of the invention.

What is claimed is:

1. A controlled release preparation of a biologically active compound comprising a reaction product obtained by reacting:

(a) a copolymer consisting essentially of maleic anhydride and at least one polyalkylene glycol ether represented by formula (I):

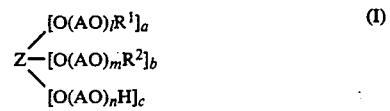

wherein Z represents the remaining residue of a compound having from 2 to 8 hydroxyl groups once all the hydroxyl groups are removed; $R^1$ represents an alkenyl group having from 2 to 5 carbon atoms; AO represents an oxyalkylene group having from 2 to 18 carbon atoms or a combination thereof which may be linked together in blocks or at random; $R^2$ represents a hydrocarbon group having from 1 to 24 carbon atoms; a represents a positive integer, b and c each represents 0 or a positive integer, and $a+b+c=2$ to 8; $l \geq 9$, $m \geq 0$, $n \geq 0$, and $l+m+n=1$ to 1000; and (b) a biologically active compound having an amino group.

2. A controlled release preparation of a biologically active compound as claimed in claim 1, wherein said biologically active compound having an amino group is an enzyme, a peptide other than an enzyme, and aminoglucoside, or a pesticide.

3. A controlled release preparation of a biologically active compound as claimed in claim 2, wherein said enzyme is a hydrolase, an oxidoreductase, an isomerase, a transferase or an eliminase.

4. A controlled release preparation of a biologically active compound as claimed in claim 2, wherein said enzyme is amylase, protease, cellulase, hemicellulase, lipase, pectinase, lysozyme, hesperidinase, anthocyanase, aminoacylase, urease, invertase, melibiase, dextranase, peptidase, ribonuclease, lactase, glucose oxidase, uricase, catalase, lipoxygenase, cytochrome C, peroxidase, glycose isomerase, cyclodextrin glucosyltransferase, transaminase, aspartase, hyaluronidase, or chondroitinase.

5. A controlled release preparation of a biologically active compound as claimed in claim 2, wherein said pesticide is 3,5-dichloroaniline or 2,6-dichloro-4-nitroaniline.

* * * * *

UNITED STATES PATENT AND TRADEMARK OFFICE
CERTIFICATE OF CORRECTION

PATENT NO. : 5,320,837

DATED : June 14, 1994

INVENTOR(S) : Shin-ichi Akimoto et al

It is certified that error appears in the above-identified patent and that said Letters Patent is hereby corrected as shown below:

Col. 8,  line 60, delete "$\ell \geq 9$", insert --$\ell \geq 0$--.

Col. 10, line 2, delete "glycose isomerase", insert --glucose isomerase--.

Signed and Sealed this

Twenty-ninth Day of November, 1994

Attest:

BRUCE LEHMAN

*Attesting Officer*   *Commissioner of Patents and Trademarks*